United States Patent
Heine et al.

(10) Patent No.: US 9,498,111 B2
(45) Date of Patent: Nov. 22, 2016

(54) OTOSCOPE WITH EJECTABLE EAR SPECULUM

(71) Applicant: Heine Optotechnik GmbH & Co KG, Herrsching (DE)

(72) Inventors: Oliver Heine, Herrsching (DE); Wolfgang Behrendt, Seefeld (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 398 days.

(21) Appl. No.: 14/134,131

(22) Filed: Dec. 19, 2013

(65) Prior Publication Data
US 2014/0171743 A1   Jun. 19, 2014

(30) Foreign Application Priority Data
Dec. 19, 2012   (DE) .................. 10 2012 223 691

(51) Int. Cl.
*A61B 1/267* (2006.01)
*A61B 1/227* (2006.01)
*A61B 1/00* (2006.01)

(52) U.S. Cl.
CPC ........... *A61B 1/227* (2013.01); *A61B 1/00142* (2013.01)

(58) Field of Classification Search
CPC .... A61B 1/227; A61B 1/2275; A61B 1/233; A61B 1/307; A61B 1/313; A61B 1/32; A61B 1/00142; A61B 1/00105; A61B 1/00101; G01J 5/021
See application file for complete search history.

(56) References Cited

U.S. PATENT DOCUMENTS

| | | | | |
|---|---|---|---|---|
| 1,686,041 A | * | 10/1928 | Smith | A61B 1/227 600/200 |
| 2,507,771 A | * | 5/1950 | Cole | A61B 1/227 600/200 |
| 3,110,304 A | * | 11/1963 | Hartman | A61B 1/227 600/200 |
| 3,146,775 A | * | 9/1964 | Moore | A61B 1/227 362/554 |
| 3,728,998 A | * | 4/1973 | Heine | A61B 1/227 385/117 |
| 3,815,584 A | * | 6/1974 | Fiore | A61B 1/32 600/184 |
| 3,840,004 A | * | 10/1974 | Heine | A61B 1/227 600/200 |
| 3,848,587 A | * | 11/1974 | McDonald | A61B 1/227 600/187 |
| 3,870,036 A | * | 3/1975 | Fiore | A61B 1/0669 600/184 |

(Continued)

FOREIGN PATENT DOCUMENTS

| | | |
|---|---|---|
| DE | 29912619 U1 | 1/2000 |
| DE | 202008005144 U1 | 6/2008 |

*Primary Examiner* — Lynnsy Summitt
(74) *Attorney, Agent, or Firm* — Bachman & LaPointe, PC (57) ABSTRACT

The otoscope includes a mounting device (14) in which an ear speculum (16) is releasably attached, the ear speculum (16) including a conically tapering cone portion (20). The ear speculum (16) includes a substantially cylindrical base portion (24) being coaxial to the cone portion (20) and having a diameter which is larger than the largest diameter of the cone portion (20) and being connected through an intermediate wall portion (22) to the cone portion (20). At least one cutout (40) extending to the free edge of the base portion (24) is formed in the base portion (24) of the ear speculum (16). A resilient snap hook (26) is arranged in the cutout (40), the resilient snap hook (26) comprising a connecting leg (60), one end of which is connected to the base portion (24) in the proximity of the free edge and which substantially extends in circumferential direction of the base portion (24), and a holding leg (64) extending from the other end of the connecting leg (60) in the direction of the intermediate wall portion (22), wherein the inner side of the snap hook (26) protrudes into the cylinder space of the base portion (24).

12 Claims, 6 Drawing Sheets

(56) References Cited

U.S. PATENT DOCUMENTS

| | | | | |
|---|---|---|---|---|
| 3,878,836 A * | 4/1975 | Twentier | A61B 1/00142 | 374/121 |
| 3,889,661 A * | 6/1975 | Fiore | A61B 1/0669 | 362/120 |
| 3,934,578 A * | 1/1976 | Heine | A61B 1/227 | 313/318.01 |
| 3,949,740 A * | 4/1976 | Twentier | A61B 1/00142 | 374/E1.013 |
| 4,993,406 A * | 2/1991 | Reynolds | A61B 1/32 | 128/DIG. 26 |
| 5,066,142 A * | 11/1991 | DeFrank | G01J 5/02 | 374/208 |
| 5,088,834 A * | 2/1992 | Howe | A61B 1/00142 | 374/158 |
| D333,702 S * | 3/1993 | Hufman | D24/135 | |
| 5,390,663 A * | 2/1995 | Schaefer | A61B 1/227 | 600/200 |
| 5,411,032 A * | 5/1995 | Esseff | G01J 5/021 | 374/121 |
| 5,415,157 A * | 5/1995 | Welcome | A61B 19/081 | 206/571 |
| 5,645,350 A * | 7/1997 | Jang | A61B 1/00142 | 374/158 |
| 5,695,448 A * | 12/1997 | Kimura | A61B 1/0005 | 600/114 |
| 5,919,130 A * | 7/1999 | Monroe | A61B 1/042 | 600/129 |
| D421,123 S * | 2/2000 | Kugler | D24/137 | |
| 6,022,140 A * | 2/2000 | Fraden | G01J 5/02 | 374/158 |
| 6,053,875 A * | 4/2000 | Rosenbaum | A61B 5/12 | 374/158 |
| 6,106,457 A * | 8/2000 | Perkins | A61B 1/00041 | 396/312 |
| 6,213,938 B1 * | 4/2001 | Cook | A61B 1/227 | 600/200 |
| 6,332,090 B1 * | 12/2001 | DeFrank | G01J 5/04 | 374/126 |
| 6,383,133 B1 * | 5/2002 | Jones | A61B 1/00105 | 600/184 |
| 6,390,975 B1 * | 5/2002 | Walls | A61B 1/32 | 600/200 |
| 6,416,464 B2 * | 7/2002 | Elliott | A61B 1/00087 | 600/184 |
| 6,432,045 B2 * | 8/2002 | Lemperle | | 600/135 |
| 6,432,046 B1 * | 8/2002 | Yarush | A61B 1/00039 | 600/109 |
| 6,554,765 B1 * | 4/2003 | Yarush | A61B 1/00039 | 348/73 |
| 6,647,284 B1 * | 11/2003 | Lee | G01J 5/021 | 374/158 |
| 7,083,330 B1 * | 8/2006 | Yao | G01J 5/0022 | 374/158 |
| 7,108,419 B2 * | 9/2006 | Harr | G01J 5/02 | 374/121 |
| 7,276,025 B2 * | 10/2007 | Roberts | A61B 1/227 | 315/312 |
| 7,354,194 B2 * | 4/2008 | Walker | G01J 5/021 | 374/158 |
| 7,354,399 B2 * | 4/2008 | Strom | A61B 1/227 | 600/200 |
| 7,399,275 B2 * | 7/2008 | Goldfain | A61B 1/00188 | 600/112 |
| 7,803,110 B2 * | 9/2010 | Goldfain | A61B 1/00188 | 600/112 |
| 7,879,009 B1 * | 2/2011 | Haddock | A61B 1/32 | 600/210 |
| D636,080 S * | 4/2011 | Goldberg | D24/137 | |
| 8,062,216 B2 * | 11/2011 | Raghuprasad | A61B 1/227 | 600/200 |
| 8,126,672 B2 * | 2/2012 | Yamaguchi | G01J 5/02 | 374/121 |
| 8,131,380 B2 * | 3/2012 | Cao | A61N 1/205 | 600/245 |
| 8,136,985 B2 * | 3/2012 | Lane | A61B 5/01 | 374/121 |
| 8,206,290 B2 * | 6/2012 | Huang | A61B 1/00052 | 600/200 |
| 8,231,271 B2 * | 7/2012 | Lane | G01J 5/0003 | 374/121 |
| 8,374,683 B2 * | 2/2013 | Stone | A61B 1/00142 | 600/179 |
| 8,403,889 B2 * | 3/2013 | Richard | A61B 17/3423 | 604/167.01 |
| 8,403,954 B2 * | 3/2013 | Santin | A61F 5/08 | 606/199 |
| 8,651,736 B2 * | 2/2014 | Mullin | G01J 5/021 | 374/158 |
| 8,876,373 B2 * | 11/2014 | Lane | G01J 5/021 | 374/121 |
| 8,882,347 B2 * | 11/2014 | Fraden | G01J 5/02 | 374/158 |
| 8,944,596 B2 * | 2/2015 | Wood | A61B 3/14 | 351/206 |
| 9,170,200 B2 * | 10/2015 | Hart | A61B 1/043 | |
| 9,198,560 B2 * | 12/2015 | Davis | A61B 1/00188 | |
| 9,261,407 B2 * | 2/2016 | Lawson | G01J 5/0003 | |
| 9,285,276 B2 * | 3/2016 | Fraden | G01K 1/08 | |
| 2001/0037050 A1 * | 11/2001 | Lemperle | A61B 1/00105 | 600/135 |
| 2002/0193665 A1 * | 12/2002 | Jones | A61B 1/00105 | 600/200 |
| 2005/0027168 A1 | 2/2005 | Strom et al. | | |
| 2006/0120432 A1 * | 6/2006 | Lantz | G01J 5/02 | 374/208 |
| 2007/0261494 A1 * | 11/2007 | Fuller | A61B 1/227 | 73/620 |
| 2009/0129437 A1 * | 5/2009 | Chuang | G01J 5/02 | 374/158 |
| 2010/0191063 A1 * | 7/2010 | Hsu | A61B 1/227 | 600/200 |
| 2011/0137118 A1 * | 6/2011 | Huang | A61B 1/227 | 600/109 |
| 2011/0166421 A1 * | 7/2011 | Katiraei | A61B 1/227 | 600/200 |
| 2011/0257521 A1 * | 10/2011 | Fraden | A61B 5/01 | 600/438 |
| 2012/0088976 A1 * | 4/2012 | Shehadeh | A61B 1/00101 | 600/187 |
| 2012/0157776 A1 * | 6/2012 | Wood | A61B 1/00039 | 600/200 |
| 2012/0203200 A1 * | 8/2012 | Kenney | A61M 1/0066 | 604/506 |
| 2012/0283517 A1 * | 11/2012 | Kirchner-Gottschalk | A61B 1/00142 | 600/200 |
| 2013/0003078 A1 * | 1/2013 | Hart | A61B 1/00082 | 356/601 |
| 2013/0023914 A1 * | 1/2013 | Truong | A61B 1/00087 | 606/162 |
| 2013/0083823 A1 * | 4/2013 | Harr | G01J 5/026 | 374/121 |
| 2013/0150675 A1 * | 6/2013 | Folley | A61B 1/227 | 600/200 |
| 2013/0190570 A1 * | 7/2013 | Hirsch | A61B 17/1697 | 600/204 |
| 2013/0245488 A1 * | 9/2013 | Quinn | A61B 5/01 | 600/549 |
| 2013/0271589 A1 * | 10/2013 | Huang | H04N 7/183 | 348/77 |
| 2013/0300919 A1 * | 11/2013 | Fletcher | H04N 5/2257 | 348/360 |
| 2013/0338678 A1 * | 12/2013 | Loushin | A61F 11/002 | 606/109 |
| 2014/0119406 A1 * | 5/2014 | Chen | G01K 1/086 | 374/209 |
| 2014/0336467 A1 * | 11/2014 | Eder | A61B 1/2275 | 600/200 |
| 2015/0250381 A1 * | 9/2015 | Bedard | A61B 1/227 | 600/200 |

(56) References Cited

U.S. PATENT DOCUMENTS

2015/0351606 A1* 12/2015 Ruppersberg ...... A61B 1/00179 600/200

2016/0058960 A1* 3/2016 Papania ............. A61B 1/00195 600/103

2016/0073875 A1* 3/2016 Goldfain .................. A61B 3/12 351/221

* cited by examiner

OTOSCOPE WITH EJECTABLE EAR SPECULUM

BACKGROUND OF THE INVENTION

The invention relates to an otoscope including a mounting device in which an ear speculum is releasably attached.

Otoscopes are used for looking into and examining the outer ear canal and usually include a light source and an optical imaging system as well as an ear speculum which is inserted into the ear canal for observation thereof.

For hygienical reasons ear specula are designed to be exchangeable, wherein it is preferable to be able to exchange an ear speculum following a patient examination without having to remove the used and possibly contaminated ear speculum by hand.

DE 20 2008 005 144 U1 discloses an otoscope including an exchangeable ear speculum, the ear speculum being attached to a speculum receptacle, wherein locking noses clampingly engage in recesses in the speculum receptacle. An ejector ring is provided for ejecting the ear speculum, the ejector ring planarly abutting against an end side of the ear speculum. The ejector ring is displaced by means of a rod system in response to the actuation of a pusher. For enabling displacement of the ear speculum by means of the ejector ring, the retention force of the locking noses in the recesses must be limited. This in turn entails that the ear speculum may come off the speculum receptacle during examination.

US 2005/0027168 A1 discloses an otoscope including an ear speculum comprising ramp-shaped engagement members at its lower edge arranged in circumferential direction about the circumference of the speculum. Upon insertion of the ear speculum in the mounting device of the otoscope the ear speculum is twisted about its longitudinal axis, whereby the ramp-like engagement members lockingly engage in corresponding receptales in the mounting device. By turning a rotary knob at the mounting device the ear speculum is rotated in the opposite direction until the engagement ramp has been moved out of the respective receptacle. Subsequently the ear speculum can be shaken off. Inserting the ear speculum in the mounting device is relatively complicated and thus requires sufficient dexterity of the examining person.

In the case of the otoscope known from US 2005/0027168 A1 as well as in the case of the otoscope disclosed in DE 20 2008 005 144 U1 the ejected ear specula can be reused. This entails the risk that patients are examined with an ear speculum which has already been used before and are exposed to a risk of infection.

The object underlying the invention is to use means of simple design for providing an otoscope including ear specula which are capable of being securely attached and detached in a simple manner, wherein it is preferable that it is impossible to reuse the ear speculum once it has been detached.

This object is achieved by an otoscope comprising a mounting device in which an ear speculum is releasably attached, said ear speculum including a conically tapering cone portion, wherein said ear speculum comprises a substantially cylindrical base portion being coaxial to said cone portion and having a diameter which is larger than the largest diameter of said cone portion and being connected through an intermediate wall portion to said cone portion;

at least one cutout extending to an free edge of said base portion is formed in said base portion of said ear speculum;

a resilient snap hook is arranged in said at least one cutout, said resilient snap hook comprising a connecting leg having a first and a second end, said first end being connected to said base portion in proximity of said free edge, said connecting leg substantially extending in circumferential direction of said base portion, and a holding leg extending from said second end of said connecting leg towards said intermediate wall portion, wherein an inner side of said snap hook protrudes into an cylinder space of said base portion;

said mounting device comprises an outer collar arranged within said base portion, against which said intermediate wall portion abuts and in which at least one marginal recess is formed through which said snap hook is passed with an inner side under resilient deformation such that after resilient reforming said snap hook engages behind said outer collar next to said marginal recess.

In the case of the otoscope according to the invention the ear speculum can be attached in a simple manner by placing the ear speculum thereon such that the base portion surrounds the outer collar and the snap hooks are passed with their inner sides through the marginal recesses at the outer collar. When the snap hooks are passed through the marginal recesses, they are resiliently deformed by bending the holding leg towards the edge of the cutout which is connected to the connecting leg. After the snap hook has been passed through the marginal recess, the holding leg is restored to its initial position and therefore engages behind the outer collar. Thus the ear speculum is securely connected to the mounting device and cannot unintentionally become detached.

In an advantageous embodiment a stopper lug is provided which protrudes from the holding leg of the snap hook outwardly in relation to the base portion. Further a rotatable device is provided which can be rotated about the longitudinal axis of the cone portion and which includes at least one recess facing the base portion and being engaged by the stopper lug. When the rotatable device is turned in the appropriate direction, the holding leg is bent back towards the direction of the edge of the cutout such that the snap hook can be passed back through the corresponding marginal recess when the ear speculum is detached.

Said detaching is facilitated if in an advantageous embodiment a through-going recess is formed adjacent to the at least one cutout in the base portion, the height of the through-going recess decreasing in relation to the free edge of the base portion in ramp-like fashion towards the cutout, and if an engagement member is mounted at the rotatable device which engages in the through-going recess. In the case of this embodiment not only the holding leg is deformed such that the snap hook fits through the marginal recess when the rotatable knob is twisted, but also the ear speculum is simultaneously raised by the engagement member sliding along the ramp-like portion and becomes detached automatically from the mounting device.

Preferably the rotatable device is formed by a rotatable knob which coaxially surrounds the base portion and at the inner circumference of which the engagement member is mounted.

In order to prevent reuse of an ear speculum which has been used before, the connecting leg includes a neck or a weakness in the material configured such that the yield point of the material of the snap hook is exceeded thereat when the snap hook is resiliently deformed once again after having reformed. This happens when for detaching the ear speculum the rotatable device is turned, causing the holding leg to be bent such that the snap hook fits through the marginal recess again.

The rotatable device can be automatically moved back to its initial position if the mounting device comprises a resilient device against the spring force of which the rotatable device can be rotated from an initial position.

Advantageously the ear speculum is an integral plastic part, preferably an injection molded part.

BRIEF DESCRIPTION OF THE DRAWINGS

Hereinafter exemplary embodiments of the invention will be described in more detail with reference to the accompanying drawings, wherein.

DETAILED DESCRIPTION

Figure 4:
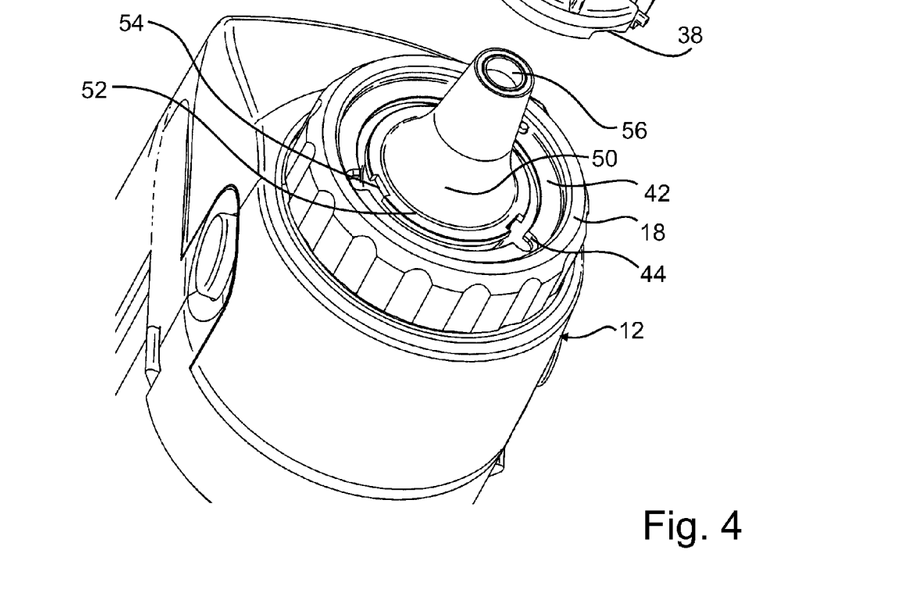
FIG. 4 is a view of the otoscope of FIG. 1 before the ear speculum is attached.

The otoscope 10 shown in FIGS. 1-8 includes a housing 12, wherein a mounting device 14 for receiving an ear speculum 16 is provided at an end side of the housing 12. As can be seen in FIG. 4, the mounting device 14 includes a substantially conically shaped speculum receptacle 50 tapering from the housing 12 and including a viewing aperture 56 at its apex, which is arranged concentrically to the observation beam path of an optical imaging system (not shown), which is accommodated inside the housing 12. An outer collar 52 is provided at the base of the speculum receptacle 50, wherein three marginal recesses 54 are formed at equal angular distances of 120° in the edge of the outer collar 52. A cylindrical basis 31 extends downwardly from the outer collar 52, wherein the outer diameter of the cylindrical basis 31 is smaller than the outer diameter of the outer collar 52. Below the cylindrical basis 31 there is a guide ring 32 attached to the end side of the housing 12 concentrically to the central axis of the speculum receptacle 50, wherein the outer diameter of the guide ring 32 is larger than the outer diameter of the outer collar 52.

A rotatable knob 18 is placed on top of the guide ring 32 such that it can be rotated about the longitudinal central axis of the speculum receptacle 50. As can be seen especially in FIG. 4, the rotatable knob 18 includes an inwardly extending annular flange 42 on a level with the outer collar 52. Marginal recesses 44 are formed in the annular flange 42, which are substantially opposite to the respective marginal recesses 54 in the outer collar 52. The inner diameter of the annular flange 42 is larger than the outer diameter of the outer collar 52.

As can be seen especially in FIG. 4, an ear speculum 16 is placed on top of the speculum receptacle 50, wherein the inner contour of the ear speculum 16 substantially corresponds to the outer contour of the speculum receptacle 50 such that upon attachment the ear speculum 16 is fixed on the speculum receptacle 50 without play.

The ear speculum 16 includes an upper cone portion 20 with a cone opening 21. An annular intermediate wall portion 22 extends outwardly from the lower end of the cone portion 20 and substantially perpendicularly to the central axis of the ear speculum 16. A cylindrical base portion 24 extends downwardly from the outer edge of the intermediate wall portion 22. Several stiffening ribs 30 are provided at the end of the cone portion 20.

Cutouts 40 are formed at angular distances of 120° in the base portion 24, which are limited by two lateral parallel side walls extending perpendicularly to the lower edge of the base portion 24. The cutout 40 thus opens into the lower edge of the base portion 24 and extends up to the intermediate wall portion 22. In each cutout 40 there is provided a snap hook 26, the design of which will be explained in more detail hereinafter.

Figure 7:
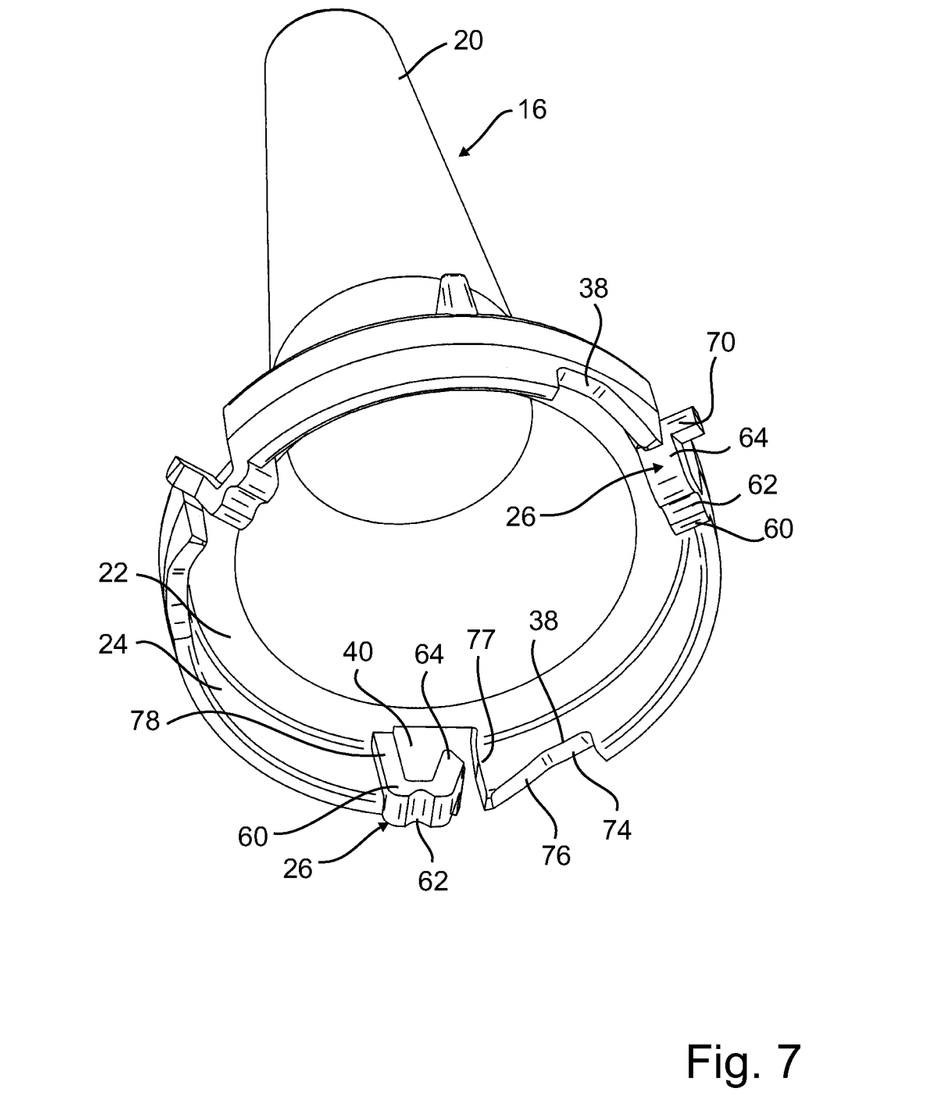
FIG. 7 is a perspective bottom view of the ear speculum of FIG. 6.

As can be seen in FIG. 7, the snap hook 26 is generally U-shaped. An inner leg 78 is configured to be flush with the left edge of the cutout 40 in FIG. 7 and extends from the lower edge of the base portion 24 up to the intermediate wall portion 22. The lower end of the inner leg 78 is joined by a connecting leg 60 extending substantially in parallel to the lower edge of the base portion 24 and circumferentially towards the direction of the side edge 77 of the cutout 40 opposite to the inner leg 78. A holding leg 64 extends upwardly at an obtuse angle from the end of the connecting leg 60 facing away from the inner leg 78 and ends in front of the side edge 77. A neck 62 is formed in the connecting leg 60, the function of which will be explained later.

Figure 8:
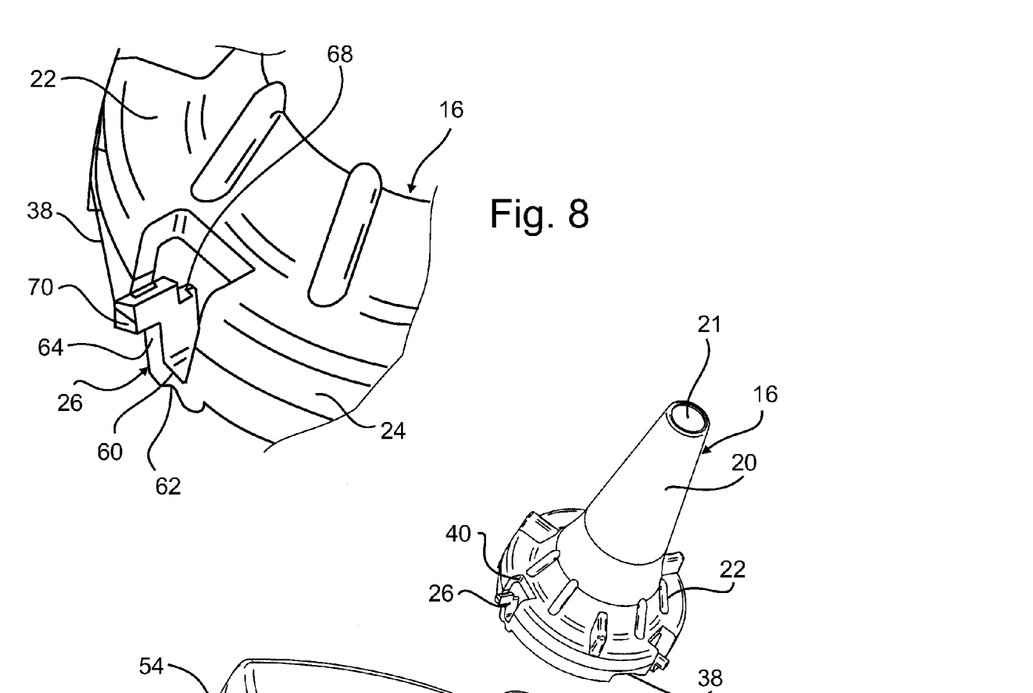
FIG. 8 is an enlarged partial view of the ear speculum in the area of a snap hook.

A stopper lug 70 is formed at the upper end of the holding leg 64 and extends outwardly beyond the outer wall of the base portion 64. In FIG. 8 it can be seen that the inner end of the stopper lug 70 ends to be flush with the inner wall of the base portion 24. As can be seen in FIG. 7, one side of the snap hook 26 protrudes inwardly beyond the inner wall of the base portion 64. The part of the free end of the holding leg 64 which protrudes inwardly beyond the inner wall of the base portion 64 is lower than the stopper lug 70, whereby a step 68 is formed.

Figure 5:
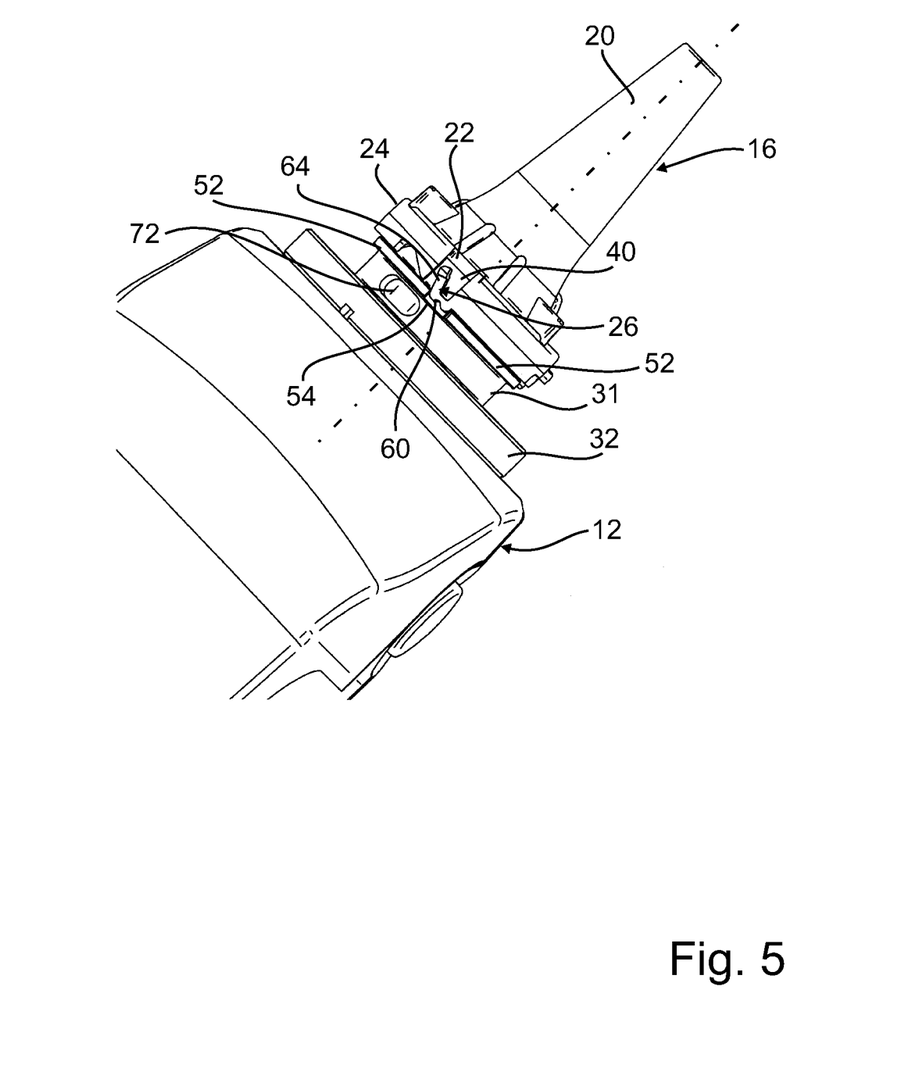
FIG. 5 is a view of the otoscope as shown in FIG. 2 just before a snap hook is introduced through a marginal recess.
Figure 6:
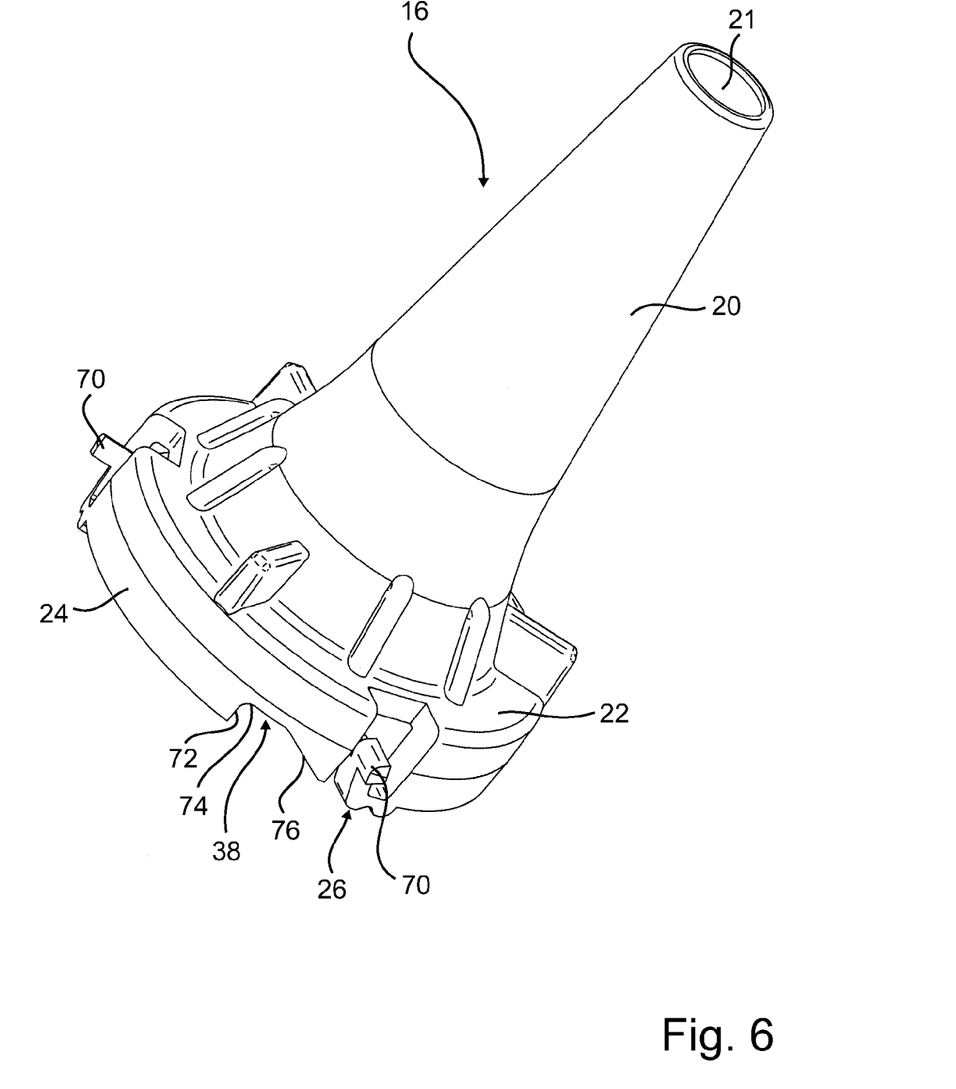
FIG. 6 is a perspective top view of the ear speculum of the otoscope of FIG. 1.

FIG. 5 shows the moment when the ear speculum 16 is placed on top of the speculum receptacle 50 such that the connecting legs 60 of the snap hooks 26 already engage in a marginal recess 54. Thereafter the ear speculum 16 is pressed downwardly, whereby the holding leg 64 is forced through the edge of the marginal recess 54 towards the direction of the inner leg 78 for enabling the holding leg 64 to pass through the marginal recess 54. As soon as the holding leg 64 has passed through the marginal recess 54, its restoring force causes the holding leg 64 to be moved back to its initial position such that it engages behind the outer collar 52.

The inner leg 78 abuts against one end of the marginal recess and thereby acts as a lock against rotation or as a counter support when detaching the ear speculum 16.

The individual elements are dimensioned such that the holding leg 64 abuts against the bottom side of the outer collar 52 when the outer collar 52 abuts against the intermediate wall portion 22. This can be best seen in FIG. 2.

Figure 1:
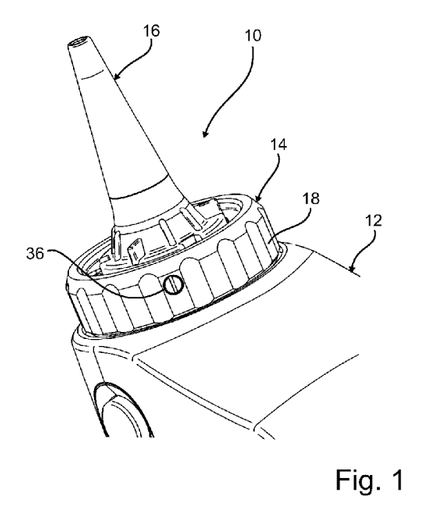
FIG. 1 is a perspective view of an otoscope in the area of the receptacle for an ear speculum.
Figure 2:
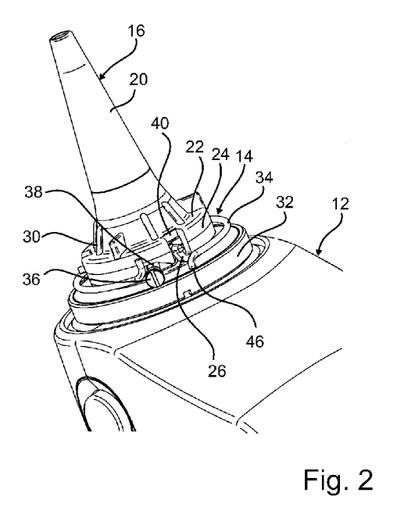
FIG. 2 is the view of FIG. 1, wherein a rotatable knob has been omitted.
Figure 3:
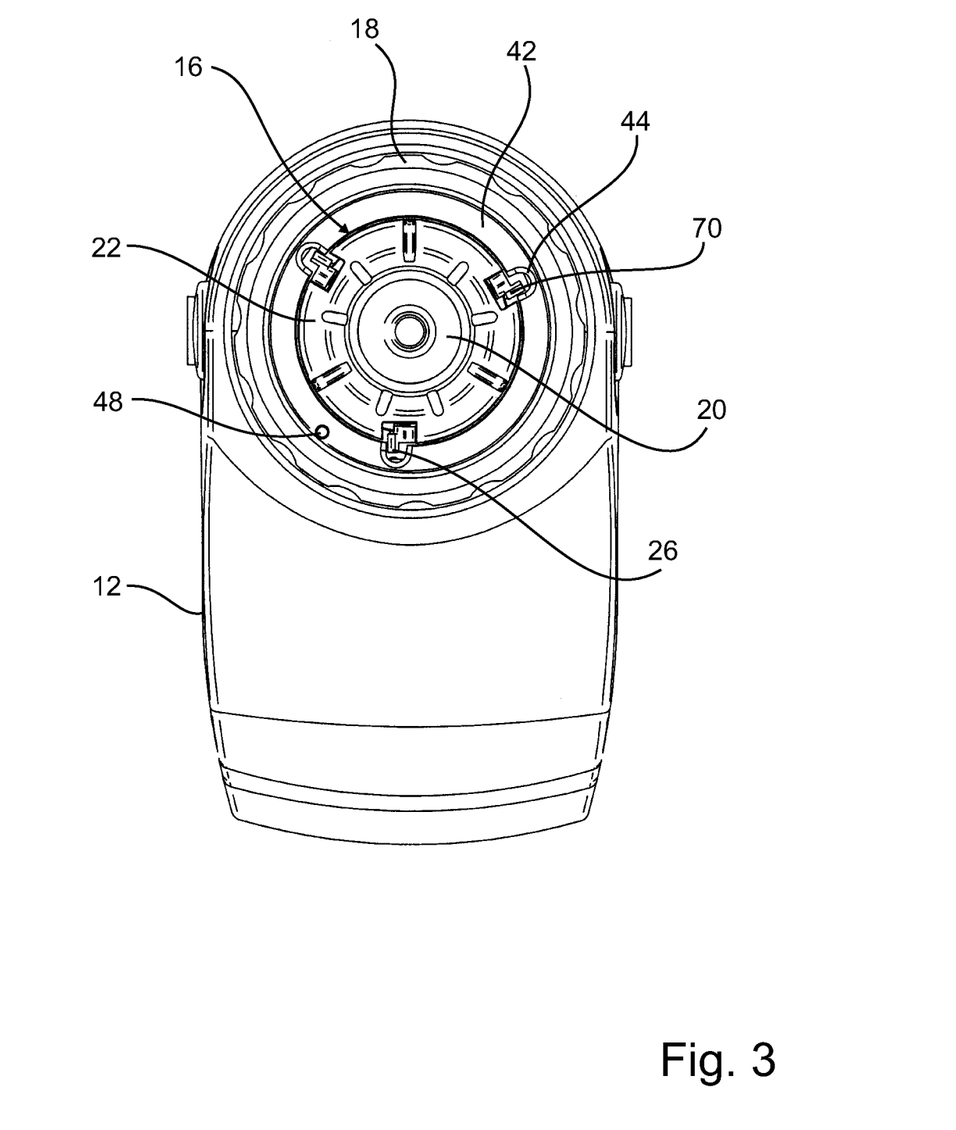
FIG. 3 is a plan view of the otoscope of FIG. 1.

As can be seen in FIG. 7, the base portion 24 includes a through-going recess 38 adjacent to the side edge 77 of the cutout 40. The height of the through-going recess 38 increases steadily in a ramp portion 76 up to a straight portion 74. FIGS. 1 and 2 show that an inwardly extending engagement bolt 36 is fixed radially in the rotatable knob 18 above the guide ring 32. The engagement bolt 36 extends through the through-going recess 38 in the base portion 24 into a long-hole recess 72 provided below the outer collar 52 behind the through-going recess 38 in the basis 31. Furthermore a circular wire spring 34 is provided, one end of which is secured in a fixing hole 46 in the guide ring and the other end of which is secured in a fixing hole 48 in the annular flange 42 of the rotatable knob 18. The circular wire spring 34 surrounds the speculum receptacle concentrically outside the base portion 24.

When the ear speculum 16 is to be exchanged, the rotatable knob 18 in FIG. 1 is turned to the right, i. e. anti-clockwise. Since the stopper lug 70 of the snap hook 26 is located in the recess 44 in the annular flange 42, during the rotation the holding leg 64 is bent towards the direction of the inner leg 78 such that the holding leg 64 is able to pass back through the corresponding marginal recess 54. Therein the inner leg 78 which abuts against the end of the marginal recess 54 acts as a counter support. During the rotation simultaneously the engagement bolt 36 is moved along the ramp portion 76 of the base portion 24 such that the ear speculum 16 is raised upwardly, enabling the ear speculum 16 to become detached from the mounting device 14 without having to be touched by hand.

By the repeated bending of the connecting leg 60 about the neck 62 the yield point of the snap hook 26 is exceeded, with the result that after removal of the ear speculum 16 the holding leg 64 is not moved back to its initial position. Thus the ear speculum 16 becomes unfit for use and needs to be replaced by a new ear speculum 16. This prevents reuse of an ear speculum 16 which has already been used before.

After ejection of the ear speculum 16 the rotatable knob 18 is moved back to its initial position by means of the wire spring 34. Subsequently a new ear speculum 16 can be releasably attached to the mounting device 14.

The invention claimed is:

1. An otoscope comprising a mounting device in which an ear speculum is releasably attached, said ear speculum including a conically tapering cone portion,
wherein
   said ear speculum comprises a substantially cylindrical base portion being coaxial to said cone portion and having a diameter which is larger than the largest diameter of said cone portion and being connected through an intermediate wall portion to said cone portion;
   at least one cutout extending to a free edge of said base portion is formed in said base portion of said ear speculum;
   a resilient snap hook is arranged in said at least one cutout, said resilient snap hook comprising a connecting leg having a first and a second end, said first end being connected to said base portion in proximity of said free edge, said connecting leg substantially extending in circumferential direction of said base portion, and a holding leg extending from said second end of said connecting leg towards said intermediate wall portion, wherein an inner side of said snap hook protrudes into a cylinder space of said base portion; and
   said mounting device comprises an outer collar arranged within said base portion, against which said intermediate wall portion abuts and in which at least one marginal recess is formed through which said snap hook is passed with the inner side under resilient deformation such that after resilient reforming said snap hook engages behind said outer collar next to said marginal recess.

2. The otoscope according to claim 1, further comprising
   a stopper lug protruding from said holding leg of said snap hook outwardly in relation to said base portion and
   a rotatable device which can be rotated about a longitudinal central axis of said cone portion and which includes at least one recess facing said base portion and being engaged by said stopper lug.

3. The otoscope according to claim 2, wherein
   a through-going recess is formed adjacent to said at least one cutout in said base portion, said through-going recess having a height decreasing in relation to said free edge of said base portion in ramp-like fashion towards said cutout, and
   an engagement member is mounted at said rotatable device which engages in said through-going recess.

4. The otoscope according to claim 3, wherein said rotatable device is formed by a rotatable knob which coaxially surrounds said base portion, said rotatable knob having an inner circumference at which said engagement member is mounted.

5. The otoscope according to claim 2, wherein said mounting device comprises resilient means having a spring force against which said rotatable device can be rotated from an initial position, the resilient means having a restoring force through which said rotatable device can be rotated back to an initial position after having been rotated.

6. The otoscope according to claim 1, wherein said connecting leg is formed of a material which includes a neck wherein a yield point of the material at the neck is exceeded at the neck when said snap hook is resiliently deformed once again after having reformed.

7. The otoscope according to claim 1, wherein said ear speculum is an integral plastic part.

8. An ear speculum for attachment to a mounting device provided at an otoscope, said ear speculum comprising a conically tapering cone portion,
wherein
   a substantially cylindrical base portion being coaxial to said cone portion and having a diameter which is larger than the largest diameter of said cone portion is connected through an intermediate wall portion to said cone portion;
   at least one cutout extending to a free edge of said base portion is formed in said base portion of said ear speculum; and
   a resilient snap hook is arranged in said at least one cutout, said resilient snap hook comprising a connecting leg having a first and a second end, said first end being connected to said base portion in proximity of said free edge, said connecting leg substantially extending in circumferential direction of said base portion, and a holding leg extending from said second end of said connecting leg towards said intermediate wall portion, wherein an inner side of said snap hook protrudes into a cylinder space of said base portion, wherein a stopper lug protrudes from said holding leg outwardly beyond a cylindrical outside of said base portion.

9. The ear speculum according to 8, wherein said connecting leg is formed of a material which includes a neck wherein a yield point of the material at the neck is exceeded at the neck when said snap hook is resiliently deformed once again after having reformed.

10. The ear speculum according claim 8, wherein said ear speculum is an integral plastic part.

11. An otoscope comprising a mounting device in which an ear speculum is releasably attached, said ear speculum including a conically tapering cone portion, wherein
said ear speculum comprises a substantially cylindrical base portion being coaxial to said cone portion and having a diameter which is larger than the largest diameter of said cone portion and being connected through an intermediate wall portion to said cone portion;
at least one cutout extending to a free edge of said base portion is formed in said base portion of said ear speculum;
a resilient snap hook is arranged in said at least one cutout, said resilient snap hook comprising a connecting leg having a first and a second end, said first end being connected to said base portion in proximity of said free edge, said connecting leg substantially extending in circumferential direction of said base portion, and a holding leg extending from said second end of said connecting leg towards said intermediate wall portion, wherein an inner side of said snap hook protrudes into a cylinder space of said base portion;
said mounting device comprises an outer collar arranged within said base portion, against which said intermediate wall portion abuts and in which at least one marginal recess is formed through which said snap hook is passed with the inner side under resilient deformation such that after resilient reforming said snap hook engages behind said outer collar next to said marginal recess;
a stopper lug protrudes from said holding leg of said snap hook outwardly in relation to said base portion; and
a rotatable device is provided which can be rotated about a longitudinal central axis of said cone portion and which includes at least one recess facing said base portion and being engaged by said stopper lug.

12. An ear speculum for attachment to a mounting device provided at an otoscope, said ear speculum comprising a conically tapering cone portion,
wherein
a substantially cylindrical base portion being coaxial to said cone portion and having a diameter which is larger than the largest diameter of said cone portion is connected through an intermediate wall portion to said cone portion;
at least one cutout extending to a free edge of said base portion is formed in said base portion of said ear speculum;
a resilient snap hook is arranged in said at least one cutout, said resilient snap hook comprising a connecting leg having a first and a second end, said first end being connected to said base portion in proximity of said free edge, said connecting leg substantially extending in circumferential direction of said base portion, and a holding leg extending from said second end of said connecting leg towards said intermediate wall portion, wherein an inner side of said snap hook protrudes into a cylinder space of said base portion; and
said connecting leg is formed of a material which includes a neck wherein a yield point of the material at the neck is exceeded at the neck when said snap hook is resiliently deformed once again after having reformed.

* * * * *